United States Patent [19]

Borch et al.

[11] Patent Number: 4,938,949

[45] Date of Patent: Jul. 3, 1990

[54] TREATMENT OF DAMAGED BONE MARROW AND DOSAGE UNITS THEREFOR

[75] Inventors: Richard F. Borch, Pittsford; Therese K. Schmalbach, Rochester, both of N.Y.

[73] Assignee: University of New York, Rochester, N.Y.

[21] Appl. No.: 243,405

[22] Filed: Sep. 12, 1988

[51] Int. Cl.$^5$ ............................................. A61K 47/00
[52] U.S. Cl. ....................................... 424/10; 514/476
[58] Field of Search ........................... 424/10; 514/476

[56] References Cited

U.S. PATENT DOCUMENTS

| | | | |
|---|---|---|---|
| 4,148,885 | 4/1979 | Renoux et al. | 514/476 |
| 4,594,238 | 6/1986 | Borch | 514/476 |
| 4,645,661 | 2/1987 | Schonbaum | 424/10 |

OTHER PUBLICATIONS

D. L. Bodenner et al, *Cancer Res.* 46, 2751–2755 (1986).
M. M. Jones et al, *Cancer Chemother. Pharmacol.* 17, 38–42 (1986).
D. A. Juckett et al, *Proc. AACR, Abstracts* 25, 322, Abstr. No. 1274 (1984).
Chemical Abstract 105(3): 17989p, Selective Protection Against Cis-Diamminedichloroplatinum (II)–Induced Toxicity in Kidney, Gut, and Bone Marrow by Diethyl-Dithiocarbamate, Bodenner et al.

*Primary Examiner*—Douglas W. Robinson
*Assistant Examiner*—Raymond J. Henley, III
*Attorney, Agent, or Firm*—Merchant, Gould, Smith, Edell, Welter & Schmidt

[57] ABSTRACT

Various types of biological treatments, including antineoplastic treatments with antineoplastic drugs, can result in damage to the blood-forming function of the bone marrow. This damage can be reversed, at least to some degree, with an effective amount (preferably an extremely low dose) of a pharmaceutically acceptable dithiocarbamic compound, including a compound of the formula $R_1R_2NCSSM$ or $R_1R_2NCSS-SCSNR^3R^4$, wherein $R^1$, $R^2$, $R^3$, and $R^4$ are the same or different aliphatic or cycloaliphatic or heterocycloaliphatic groups, unsubstituted or substituted by hydroxyl, or one of $R^1$ and $R^2$ and one of $R^3$ and $R^4$ can be H, or $R^1$ and $R^2$ or $R^3$ and $R^4$, taken together with the N atom upon which the pair of R groups is substituted, can be a 5- or 6-member N-heterocyclic ring which is aliphatic or aliphatic interrupted by a ring oxygen or second ring nitrogen, and M is H or one equivalent of a pharmaceutically acceptable cation, in which case the rest of the molecule is negatively charged. The dosage in mammals can range from about 0.001 to 30 mg/kg of body weight. For larger mammals, including humans, a typical dosage unit is less than 10 mg/kg, e.g. <3 mg/kg. The dosage unit can be dissolved in a suitable pharmaceutically acceptable carrier (e.g. an aqueous medium) and is then preferably administered intravenously within 8 hours of the administration of the agent which can cause bone marrow damage. The extremely low dosages particularly preferred in this invention do not cause any significant side effects.

2 Claims, No Drawings

TREATMENT OF DAMAGED BONE MARROW AND DOSAGE UNITS THEREFOR

FIELD OF THE INVENTION

This invention relates to a method for the treatment of damage to the blood-forming function of the bone marrow of a living mammal. An aspect of this invention relates to the treatment of bone marrow which has been damaged as a result of the undesirable side effects of anti-cancer treatments or the like, particularly damage caused by the bone marrow toxicity of anti-cancer drugs. Another aspect of this invention relates to the alleviation of the dose-limiting aspects of certain clinical treatments, particularly anti-cancer treatments in which the blood-forming function of the bone marrow is impaired. A still further aspect of this invention relates to unit dosages for the parenteral administration of compounds found to be effective in restoring, at least partially, the blood-forming function of bone marrow damaged by clinical treatments for cancer or other diseases.

BACKGROUND OF THE INVENTION

At least as far back as the early 1970's, it was found that dithiocarbamates and their dimers (e.g. disulfiram) are clinically-useful compounds of relatively low toxicity toward mammals. One of the early uses of sodium diethyldithiocarbamate was in the treatment of acute nickel carbonyl poisoning. See S. William Sunderman, Ann. Clin. Res. 3:182–185 (1971). The diethyldithiocarbamate dimer, disulfiram has been used to treat alcoholism. More recently, dithiocarbamates or their dimers have been used to inhibit the undesirable side effects of platinum compounds such as the square planer platinum (II) complexes used as antineoplastic agents. See U.S. Pat. Nos. 4,426,372 (Jan. 17, 1984), 4,594,238 (June 10, 1986), and 4,581,224 (Apr. 8, 1986), all issued to R. F. Borch. For a discussion of the types of platinum-containing drugs contemplated by Borch for use in combination with these dithiocarbamic compounds, see (in addition to the three Borch patents) U.S. Pat. No. 4,053,587 (Davidson et al), issued Oct. 11, 1977, 4,137,248 (Gale et al), issued Jan. 30, 1979, 4,562,275 (Speer et al), issued Dec. 31, 1985, 4,680,308 (Schwartz et al), issued July 14, 1987, and similar references appearing in both the patent and scientific literature, e.g. the series of papers regarding platinum treatment of tumors and resulting side effects in Cancer Treatment Reports, volume 63 (1979), beginning at page 1433. The platinum compounds useful as antineoplastic agents are not limited to platinum (II) compounds, because it has been found that platinum (IV) compounds can be administered in much the same manner as platinum (II) compounds, apparently because these six-ligand complexes break down in vivo to square planar complexes of the platinum (II) type.

The Borch method of, for example, U.S. Pat. No. 4,426,372 has been shown to be effective in clinical trials. That is, this method reduces substantially the side effects of platinum-containing drugs. These side effects include both kidney toxicity and bone marrow toxicity. The mechanism by which dithiocarbamic compounds protect against or reduce the kidney toxicity has been studied extensively by Borch and his co-workers and has even been simulated accurately with in vitro studies. Accordingly, this mechanism is relatively well understood. To reverse or prevent kidney toxicity, the dithiocarbamic compound is administered after the platinum-containing drug has already begun to attack the tumor (the beneficial effect of the drug) and also has begun to attack critically important structures within the kidney (the undesirable side effect). The thus-administered dithiocarbamic compound does not reverse the tumor inhibition effects of the platinum drug, but it does displace platinum from these critical structures within the kidney, resulting in the formation of relatively harmless dithiocarbamate/Pt complexes, some of which are eliminated in the urine. This reversal of kidney damage appears to take place through a relatively straightforward chemical reaction requiring stoichiometric or nearly stoichiometric amounts of dithiocarbamic compound with respect to the amount of platinum tied up in the kidney. As a result, the effective dose of dithiocarbamic compound in the Borch method tends to reflect the stoichiometry of the situation and, for 5 mg/kg of intravenously administered platinum compound, the amount of dithiocarbamic "rescue agent", in mice, is likely to be in the range of 100 mg/kg to 400 mg/kg (intravenously) and can range as high as 750 mg/kg (intraperitoneally), also in mice. A dosage of less than 50 mg/kg of body weight of dithiocarbamate is not likely to be fully effective in providing relief from or prevention of kidney damage.

Although pharmaceutically acceptable dithiocarbamic compounds such as sodium diethyldithiocarbamate (NaDDTC) and disulfiram have relatively high $LD_{50}$ values and are not considered highly toxic to mammals, there are scattered reports in the literature regarding strange behavior exhibited by rats or mice injected with NaDDTC. The true import of these scattered disclosures and suggestions in the literature became fully apparent during clinical trials of NaDDTC as a "rescue agent", i.e. as an agent for the reduction of side effects from the administration of platinum compounds. These clinical trials demonstrated that human patients given dosages of NaDDTC effective for "rescue" purposes (e.g. dosages on the order of 50–150 mg/kg of body weight) experienced extremely unpleasant effects which caused them to feel panic and discomfort. It was necessary to develop a technique of administration of the NaDDTC whereby the patient would be sedated prior to receiving the dithiocarbamate.

All available evidence indicates that the panic reaction to dithiocarbamates resulting from dosages of, for example, 50–150 mg/kg is not the result of any life-threatening process occuring in the body of the patient, nor is there any evidence of permanent or chronic effects or damage resulting from NaDDTC administration. After the course of dithiocarbamate administration has been completed, patients returned to normal and no sequellae of the panic reaction are observed. Moreover, it presently appears that some hydroxy-substituted analogs of NaDDTC may be even less toxic than NaDDTC itself.

Nevertheless, further improvement in the treatment of toxic side effects (e.g. treating the side effects of platinum compounds) is desirable.

As noted previously, much less is known about treatments for bone marrow toxicity. Some anti-cancer drugs, both platinum-containing and platinum-free, can seriously damage the blood-forming function of the bone marrow - an effect sometimes referred to as myelosuppression. Among the drugs causing significant myelosuppression effects are cytotoxic antibiotics and antibiotic derivatives, other cytotoxic drugs, antimetabolites (which inhibit processes involved in DNA formation), alkaloid-type anti-tumor agents, alkylating agents, and heavy metal complexes (particularly Pt complexes such as "Carboplatin"). A treatment for the side effects of these drugs would be a highly welcome addition to the field of cancer treatment.

Radiation therapy is still another potential source of serious damage to the blood-forming function of the bone marrow. Administration of various compounds (such as dithiocarbamates) has been studied as a preventative treatment for the side effects of radiation therapy.

Various sulfur-containing compounds including NaDDTC have been suggested as immunostimulant medicines. See U.S. Pat. No. 4,148,885 (Renoux et al), issued Apr. 10, 1979.

SUMMARY OF THE INVENTION

It has now been discovered that dithiocarbamic compounds of the formula

wherein $R^1$ and $R^2$ are the same or different lower aliphatic or cycloaliphatic or heterocycloaliphatic groups, unsubstituted or substituted by hydroxyl, or one of $R^1$ and $R^2$, but not both, can H, or $R^1$ and $R^2$, taken together with the N atom, can be a 5- or 6-member N-heterocyclic ring which is aliphatic or aliphatic interrupted by a ring oxygen or a second ring nitrogen, and M is H or one equivalent of a pharmaceutically acceptable cation, in which case the rest of the molecule is negative charged, or
M is

wherein $R^3$ and $R^4$ are defined in the same manner as $R^1$ and $R^2$, are surprisingly effective for the treatment of damage to the blood-forming function of the bone marrow of a living mammal when administered in very low doses which do not cause the panic response described previously. Amounts of dithiocarbamic compound in excess of 30 mg/kg of body weight of small mammals (e.g. mice) are not needed in this invention, and would be very excessive for large mammals such as humans particularly in the case of damage caused by platinum-containing drugs. At least some beneficial response to the dithiocarbamic compound is observable even in small mammals at dosage levels in the microgram/kg range. Thus, a suitable dosage unit according to this invention can be in the range of about 0.001 to 30 mg per kilogram of body weight of the mammal, more preferably above about 0.003 and up to about 10 mg/kg of body weight.

The therapeutic effect of the dithiocarbamic compounds described above is not limited to treating damage caused by platinum-containing drugs. Mammals given platinum-free myleosuppressive antineoplastic drugs can also be successfully treated with an effective amount of one of these dithiocarbamate salts or dimers (or, less preferably, acids, i.e. where M=H). The preferred dosage units for treating the side effects of these platinum-free drugs are the same as for the platinum-containing drugs, but dosages up to 300 mg/kg in mice (up to 75 mg/kg in humans) appear to be tolerated when adequate precautions are utilized, e.g. sedation.

As will be explained subsequently, guidelines for converting these dosage units into mg/m² have been discovered, both for large mammals, such as humans, and small mammals, such as mice. In principle, mg/m² dosing is equivalent in all species, including both large and small mammals. It has also been found that the gap between a suitable mg/kg dosage unit for a small mammal and a suitable mg/kg dosage unit for a human is somewhat less than might have been predicted by a skilled pharmacologist.

These very low dosages are believed to be well below stoichiometric levels and bear more resemblance to amounts at which catalysts are employed. Surprisingly, improvement in the blood-forming function of normal bone marrow is rather minimal when the dithiocarbamic compounds of this invention are administered to a healthy mammal. However, very significant improvements in bone marrow function are observed when the bone marrow of the mammal has been damaged, e.g. by administration of anti-cancer drugs. Accordingly, the method of this invention applies primarily to mammals who have already suffered some myelosuppression effects. However, because there may be some time delay involved in observing the beneficial effects of this invention, it is possible to administer the dithiocarbamic compound more or less simultaneously with the myelosuppression-causing agent (i.e. the drug or radiation or the like). Typically, the dithiocarbamic compound will be administered after the myelosuppression-causing agent has been given to the patient.

The preferred dithiocarbamic compounds used in this invention are those of the aforementioned formula $R_1R_2NCSSM$, wherein M is a pharmaceutically acceptable cation, and $R_1$ and $R_2$ are lower aliphatic or hydroxy-substituted lower aliphatic groups (e.g. a polyhydroxy-substituted $C_6$-alkyl group). The preferred route of administration of these compounds (particularly when M is a metallic cation) is intravenous, and a suitable unit dosage can be dissolved, suspended, or otherwise combined with a pharmaceutially acceptable carrier such as an aqueous medium. In the case of the dimers (e.g. disulfiram), which are far less water soluble, the preferred route of administration is oral.

DETAILED DESCRIPTION

Most of the discussion which follows is related to the use of dithiocarbamates to protect against the bone marrow toxicity of anti-cancer drugs. However, it will be understood that the method of this invention can find application whenever the blood-forming function of the bone marrow of a living mammal has been damaged. As noted previously, clinical use of the method and dosage units of this invention can be carried out in combination with known antitumor agents and can be more or less simultaneous with (or even previous to) the administration of the antitumor agent, although typically the antitumor agent will be administered first. It is generally desirable that, when the antitumor agent is administered first, the dithiocarbamate is given to the treated mammal within 6 or 8 hours.

Myelosuppression (toxicity to the blood-forming cells of the bone marrow) is a serious and frequently dose-limiting side effect of most cancer drugs used in the cancer clinic today. Because these are rapidly dividing cells, they are particularly succeptible to the toxic effects of drugs used to control diseases of cell proliferation. The stem cell is the most primitive of the bone marrow cells; it represents less than 0.1 % of the cells of the marrow, yet it is capable of differentiating to produce progenitor cells for all of the blood cell lines (red cells, lymphocytes, granulocytes, and platelet precursors). The stem cell is also a self-replenishing cell in that it can undergo division to generate additional stem cells. Although stem cells have only recently specifically isolated and characterized, and then only in mice, an estimate of their numbers can be obtained using the spleen colony assay (CFU-S). Maintenance of an appropriate population of stem cells is obviously critical to survival of mammals and perhaps other organisims.

The granulocyte precursor is one of the most important and frequently damaged progenitor cell in the bone marrow. Its clinical importance lies in the role that the granulocyte plays in fighting infections. Patients with markedly reduced granulocyte counts resulting from cancer chemotherapy are highly susceptible to infection from a variety of organisms and, if bone marrow function does not recover quickly enough, they can succumb to infection rather than the primary malignancy for which they have been receiving treatment. The granulocyte precursor derives from differentiation of a stem cell; this precursor can also replicate itself by division or undergo subsequent differentiation to produce a mature granulocyte. The granulocyte precursor is more abundant in the marrow than the stem cell, and its numbers can be estimated using the CFU-GM assay.

As noted previously, the mechanism involved in the method of this invention appears to be unique and was apparently not known as of the time this invention was made. Mechanistic studies done in connection with this invention reveal that anticancer drugs which inhibit tumor growth through interference with DNA synthesis (and which have the unfortunate effect of interfering with DNA synthesis in bone marrow also) are significantly modulated in their effect upon DNA synthesis in bone marrow when the dithiocarbamate is administered after the anti-cancer drug, e.g. three hours afterward. Although this invention is not bound by any theory, these results have been interpreted as showing that the mechanism of bone marrow protection provided by the dithiocarbamates is different from that involved in the reversal of other toxicities (e.g. kidney toxicity) and is not dependent upon stoichiometric displacement of platinum from biochemical structures. For example, it is theorized that the dithiocarbamate stimulates proliferation of bone marrow cells that have been damaged by toxic drugs, even though present findings indicate that such stimulation does not occur to any great extent in healthy bone marrow.

TREATABLE BONE MARROW DAMAGE

As noted previously, antineoplastic agents and treatment techniques are a particularly important cause of myelosuppression. These antineoplastic treatments fall into two broad categories: radiation therapy and drugs. The drugs which have adverse effects upon blood formation (e.g. bone marrow toxicity) fall into several categories including cytotoxic antibiotics isolated from cultures of various species of Streptomyces and derivatives of such antibiotics, other cytotoxic agents which are not necessarily antibiotic derivatives, antimetabolites such as 5-fluorouracil, alkaloid-type compounds including alkaloids extracted from natural sources such as the periwinkle plant and similar herbs, DNA synthesis inhibitors and DNA crosslinkers which can be, for example, alkylating agents or heavy metal complexes (such as the platinum complexes discussed previously), and compounds containing the 2-chloroethyl group (typically a 2-chloroethyl group attached to a nitrogen atom). There are compounds presently in clinical use which fall into more than one of these categories. For example, an antibiotic derivative or a 2-chloroethyl-containing compound or a cytotoxic agent can be a DNA synthesis inhibitor and/or an alkylating agent.

"Adriamycin" (Doxorubicin hydrochloride) is perhaps a typical example of a Streptomyces-produced antibiotic derivative which is known to cause bone marrow suppression effects, primarily of leukocytes, hence careful hematologic monitoring is required when this drug is being administered to produce regression in neoplastic conditions.

There is a considerable variety of antineoplastic agents which have the 2-chloroethyl (i.e. the beta-chloroethyl) group, typically attached to a nitrogen atom. Some of these compounds are derivatives of L-amino acids, some are derivatives of steroids, some are monocyclic compounds, some are aliphatic amine derivatives, and still others are urea derivatives (including nitrosourea derivatives). Compounds of the nitrosourea type typically have the following formula:

$$Cl-CH_2CH_2-N(NO)-CO-NH-R^*$$

wherein R* is an organic group such as an aliphatic or cycloaliphatic radical or a second 2-chloroethyl group. One widely used compound of this type is 1-3-bis(2-chloroethyl) 1-nitrosourea, also known as BCNU or BiCNU or carmustine.

In antineoplastic drugs containing the 2-chloroethyl group, the bis-(2-chloroethyl)-amino functional group is particularly common. This bis-substituted group has the formula $(ClCH_2CH_2)_2N-$ and can be substituted directly on an aliphatic chain or an aromatic or cycloaliphatic or heterocycloaliphatic ring (or indirectly whereby the N is part of a carbamate linkage or the like). The so-called "nitrogen mustard" derivatives typically contain the bis-(2-chloroethyl)-amino group and can be highly toxic and even hazardous if not carefully administered.

Of the agents which inhibit DNA synthesis or crosslink DNA molecules, the platinum (II) and (IV) compounds are among the most promising for clinical use. The compound "cisplatin" (cis-dichlorodiammine platinum [II]) is very effective against testicular and ovarian tumors but has been found to have myelosuppressive effects in 25-30% of patients treated with this drug. More recent developments in platinum (II) and platinum (IV) anticancer drugs have produced compounds which are not only very effective against tumors but are also substantially free of side effects other than myelosuppression. (Cisplatin, on the other hand, has significant kidney toxicity effects as well as possible bone marrow toxicity effects.)

According to the literature, preferred antitumor Pt(II) or Pt(IV) complexes (a) are neutral, (b) contain at least one pair of cis-leaving groups (generally of intermediate lability, e.g. halogens, oxalates, malonates, and other bidentate dicarboxylic acids), (c) two other cis-ligands which are preferably neutral and more or less inert. The platinum (IV) compounds can be functionally similar to the platinum (II) compounds, particularly when they are converted in vivo to the platinum (II) analogs. The platinum (IV) compounds have a coordination number of 6 and can be considered to be square planar complexes with ligands above and below the plane, forming an octahedral structure.

Platinum (II) compounds known to have some bone-marrow toxicity in a significant percentage of case have the formula

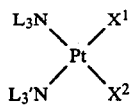

wherein $X^1$ and $X^2$ are the same or different and represent anionically ionizable leaving groups, or, taken together, $X^1$ and $X^2$ can constitute a cyclic difunctional leaving group such as a cyclic dicarboxylic acid; and $L_3$ and $L_3'$ are the same or different and represent the residues of ammine or amine ligands, or, in combination, $L_3$ and $L_3'$ together represent the residue of an aliphatic or cycloaliphatic diamine ligand.

So long as the cis-leaving groups ($X^1$ and $X^2$ in the structural formula previously set forth) are better leaving groups than ammonia, amines, and similar nitrogen-containing ligands, the exact nature of $X^1$ and $X^2$ does not appear to be critical. (It is desirable that $X^1$ and $X^2$ form physiologically acceptable anions when displaced from the platinum complex.) Accordingly, in addition to the leaving groups described previously, sulfato, sulfate, and neutral water molecules have been employed as ligands in these compounds. The hydroxyl group can serve as a leaving group when it is protonated to form a water ligand; hence, OH groups have also been employed as ligands.

Of the nitrogen-containing monodentates and bidenates myelosuppression can occur when the ligands include ammonia, diaminocyclohexane and its derivatives, alkylene diamines (e.g. ethylenediamine), alkyl-substituted amines, $C_3$ and $C_5$-cycloalkyl amines, and the like. Suitably selected tetra-valent Pt complexes such as "CHIP" can behave like Pt(II) complexes after administration to a living organism. Removal of axial ligands in vivo accounts for the Pt(II)-like activity, at least to some extent. Such tetravalent Pt complexes can be considered to be compounds of the formula

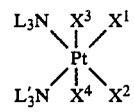

wherein $L_3$, $L_3'$, and $X^1$ and $X^2$ are as defined previously, and, as in the structural formula of the Pt(II) complexes described previously, are equatorial substituents of a square-planar complex. The equatorial $X^1$ and $X^2$ substituents are preferably halogens, e.g., Cl. The axial substituents $X^3$ and $X^4$ are the same or different and are similar to $X^1$ and $X^2$ (e.g., halogen, hydroxyl, carboxyl, sulfato, sulfate and neutral water molecules) but are preferably hydroxyls or water molecules. In these Pt(IV) complexes, $L_3N$ and $L_3'N$ are preferably aliphatic amine-type ligands such as $RNH_2$, where R is lower alkyl. A particular preferred species of Pt(IV) complex is chlorohydroxy-isopropylamineplatinum ("CHIP").

"CHIP", like other "second-generation" platinum-containing therapeutic agents is low in kidney toxicity compared to the "first generation" agents but, unfortunately, is high in bone marrow toxicity.

Various Pt(II) compounds of demonstrated anti-tumor utility, e.g., "TNO.6" and "CBDCA." (see U.S. Pat. No. 4,137,248) also show increased bone marrow toxicity. These otherwise desirable Pt(II) compounds can be characterized by the formula

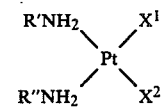

where $X^1$ and $X^2$ are the same or different and are halogen, OH, water, carboxyl, sulfato, or sulfate, or, taken together, the residue of a polycarboxylic acid; $X^1$ and $X^2$ preferably are

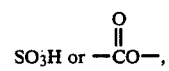

particularly as the residue of a polycarboxylic acid such as 1,1-cyclobutane acid, trimellitic acid, etc.; R' and R" are the same or different and are halogen or an aliphatic group or, taken together, the aliphatic residue of a heterocyclic moiety which includes both N-atoms.

Accordingly, there is a clear need for the treatment of damage to bone marrow when Cisplatin or any of the six following anti-tumor agents is administered to a mammal:

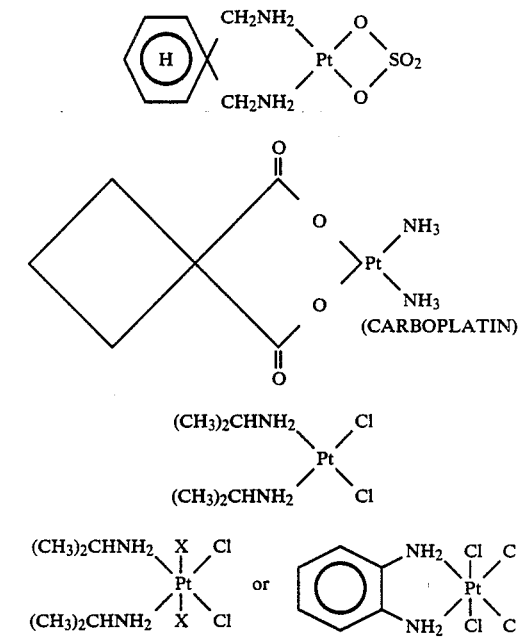

DITHIOCARBAMIC COMPOUNDS

The term "dithiocarbamic compounds" as used in this application is intended to refer to compounds containing the functional group $R_1R_2N-CS-S-$, wherein $R_1$ and $R_2$ are the same or different and represent different aliphatic or cycloaliphatic or heterocycloaliphatic groups, unsubstituted or substituted by hydroxyl. One of the two groups $R_1$ and $R_2$, but not both, can be hydrogen. Alternatively, $R_1$ and $R_2$, taken together with the N-atom, can be a 5- or 6-member N-heterocyclic ring which is aliphatic or aliphatic interrupted by a ring oxygen or a second ring nitrogen.

When the group $R_1R_2N$—CS—S— is part of a dimer such as disulfiram, the dangling valence bond is linked to a group of the formula —S—CS—N—$R_3R_4$, wherein $R_3$ and $R_4$ are defined in the same manner as $R_1$ and $R_2$. When the group $R_1R_2N$—CS—S— is an anion, the cation can be of the ammonium-type or can be derived from a monovalent or divalent metal such as an alkali or alkaline earth metal, cations which provide good water solubility and low toxicity being preferred, e.g. $Na^+$, $K^+$, $Zn^{++}$ and the like. In the case of the dithiocarbamic acids, the group $R_1R_2N$—CS—S— is linked to a hydrogen atom which is ionizable, particularly at a pH above about 5. Since the dithiocarbamic acids are not very stable in vitro, it would appear to be only marginally operative, and not advantageous, to use the dithiocarbamic acid form of the myelosuppression treatment agents of this invention. However, these acids are generally soluble in polar organic solvents such as alcohol, and they would have some tendency to form stable alkali metal salts in body fluids.

Dithiocarbamates and related compounds have been reviewed extensively in a work by G. D. Thorn et al entitled "The Dithiocarbamates and Related Compounds", Elsevier, New York, 1962. As explained in Chapter 2 of Thorn et al, the preparation of dithiocarbamates is very simple. The compounds of the formula $R_1R_2NCSSH$ or $R_1R_2NCSSNa$ can be formed by reaction of carbon disulfide with a secondary amine, typically in alcoholic or aqueous solution. The usual practice is to carry out this reaction in the presence of NaOH, so that the sodium dithiocarbamate salt is formed. Thus, for example, sodium dimethyl dithiocarbamate is formed from $CS_2$, NaOH and dimethylamine. See Thorn et al, page 14, and the references cited therein. Other typical dithiocarbamic compounds disclosed and characterized in Thorn et al include: N-methyl, N-ethyldithiocarbamates, hexamethylenedithiocarbamic acid, sodium di(beta-hydroxyethyl) dithiocarbamate, various dipropyl, dibutyl and diamyl dithicarbamates, sodium N-methyl, N-cyclobutylmethyl dithiocarbamate, sodium N-allyl-N-cyclopropylmethyldithiocarbamate, cyclohexylamyldithiocarbamates, dibenzyl-dithiocarbamates, sodium dimethylene-dithiocarbamate, various pentamethylene dithiocarbamate salts, sodium pyrrolidine-N-carbodithioate, sodium piperidine-N-carbodithioate, sodium morpholine-N-carbo-dithioate, alpha-furfuryl dithiocarbamates and imadazoline dithiocarbamates.

Another interesting type of dithiocarbamate which appears to have significant bioavailability and biocompatibility includes compounds wherein $R_1$ of the structure $R_1R_2N$—CS—S— is a hydroxy-substituted or, preferably, a polyhydroxy-substituted lower alkyl group having up to 6 carbon atoms. For example, $R_1$ can be HO—$CH_2$—CHOH—CHOH—CHOH—CHOH—$CH_2$—. In such compounds, $R_2$ can be H or lower alkyl (unsubstituted or substituted with one or more hydroxyl groups). Steric problems can, of course, be minimized when $R_2$ is H, methyl, or ethyl. Accordingly, a particularly preferred compound of this type is an N-methyl-glucamine dithiocarbamate salt, the most preferred cations of these salts being sodium or potassium.

The term "lower" (as in "lower alkyl" or "lower aliphatic"), as used in this discussion, refers to radicals having one to six carbon atoms. Water solubility and/or biocompatibility problems can be greatly increased when the number of carbon atoms exceeds six. Of the unsubstituted alkyl groups, the ethyl radical appears to provide a high level of water solubility coupled with relatively low toxicity. Nevertheless compounds such as sodium diethyldithiocarbamate (NaDDTC) are not necessarily well tolerated by humans and other mammals (even smaller mammals) when administered at levels above 50 mg/kg of body weight. Patients complain of flushing and tightness in the chest during infusion of NaDDTC, and they develop symptoms of acute anxiety. These symptoms subside rapidly and without sequelae after the infusion is stopped, and the symptoms can be alleviated somewhat (but not abolished) by pretreatment with sedatives. In the scientific literature, there are occassional references to analogous effects in rats, and these effects are sometimes referred to as the "rat rage" syndrome. A major advantage of this invention is that the "rat rage" syndrome can be avoided entirely due to the surprising efficacy of dosage units of this invention.

The dithiocarbamate derivative of N-methyl glucamine (e.g. sodium N-methylglucamine dithiocarbamate) was synthesized in 1984 and has been shown to inhibit the nephrotoxicity of the compound "cisplatin" (cis-dichlorodiammine platinum [II]). Moreover, the polyhydroxylated side chain appears to reduce somewhat the dithiocarbamate side effects described above.

Other preferred dithiocarbamates include the alkali or alkaline earth metal salts wherein the anion is di-n-butyldithiocarbamate, di-n-propyldithiocarbamate, pentamethylenedithiocarbamate, and tetramethylene dithiocarbamate and those compounds wherein $R_1$ and/or $R_2$ of the formula $R_1R_2N$—CS—S— is beta-hydroxyethyl. Generally speaking, the greater the solubility in polar solvents (particularly in aqueous media) the more convenient the administration of the dithiocarbamic myelosuppression treatment agent can be, because parenteral administration is particularly preferred in the method of this invention, and solutions (particularly aqueous solutions) are more convenient to administer than suspensions.

For this reason, the monomeric dithiocarbamic compounds are preferred over the dimeric analogs. Disulfiram is commercially available and has been used in the treatment of alcoholism to help the patient remain in a state of self-imposed sobriety. However, this alcoholism treatment is carried out by oral administration of disulfiram in tablet form. Disulfiram has relatively low solubility in polar solvents, whereas diethyldithiocarbamate monomeric salts and hydroxy-substituted alkyl dithiocarbamate monomeric salts are highly soluble in water, e.g. in molar quantities, and are also soluble in alcohol.

Other parenteral modes of administration can be used, e.g. intramuscular injection or introduction through the intraperitoneal route. However, the dosage units of this invention are most effective by the intravenous route.

DOSAGE UNITS AND FORMS

It is very common in pharmacology to express dosage units in mg/kg (i.e. mg/kg of body weight) or, if a continuing series of doses over many days is contemplated, mg/kg per day. A mg/kg dosage unit is reasonably constant for any given species of mammal. However, an average effective dose can vary from species to species, due to differences in metabolic rates. Smaller mammals such as rats and mice metabolize drugs (convert the drugs to other compounds in vivo) more effectively than larger mammals such as dogs and humans. Theoretical studies of drug metabolic rates in general tend to confirm that there is a rough inverse correlation between drug metabolic rate and the surface area of the body of the mammal. In principle, then, a dosage expressed in mg/m$^2$ would be roughly equivalent in all species, regardless of body area, i.e. an $ED_{50}$ of 100 mg/m$^2$ in a human would also be 100 mg/m$^2$ in a mouse. To convert mg/kg to mg/m$^2$, one multiplies by a constant for the desired species which is a function of the surface area of a member of that species, thus:

Dose in mg/m$^2$ = Constant × dose in mg/kg.

The constants for human, dog, rat and mouse species are, respectively; 37, 20, 5.2, and 3.0. Expressed in relative terms, the human constant is almost twice the dog constant (1.9), the human constant is over 7 times the rat constant, and the human constant is 12.3 times the mouse constant. The dosage unit for NaDDTC administered to mice to ameliorate the kidney toxicity of Cisplatin (750 mg/kg, preferably >200 mg/kg) works out to be, for example, 3.0×200 mg/kg=600 mg/m$^2$, more typically 3.0×300 mg/kg=900 mg/m$^2$. Theoretically, then, the typical human dosage unit would be 900 mg/m$^2$ divided by 37=about 25 mg/kg. In other words, theory would predict that the human dose in mg/kg would be about one twelfth of the dose for mice. In actual practice, however, it has been found that the human dose of NaDDTC can be as much as a sixth to a third, e.g. one-fourth of the dose for mice; hence, a dose in mice of, for example, 30 mg/kg works out in practice to be 5 to 10 mg/kg, most typically 7.5 mg/kg, for humans. In the present invention, a dosage of 0.003 mg/m$^2$ can provide some useful effect in humans and has even been observed to show some bone marrow-restoring effect in mice. A reliable effective does range is, for example, about 0.03 to about 145 mg/m$^2$, more preferably 130 mg/m$^2$, regardless of species. For all species, the dosage of 130 mg/m$^2$ is ample and may be unnecessarily large. Suitable dosage units can be less than 90 mg/m$^2$ or, if desired, less than 75 mg/m$^2$. For humans, dosage units in mg/kg are best calculated by dividing the mg/kg dose for mice by about 4 (instead of by 12.3). Accordingly, a dose for mice of, say, 30 mg/kg would work out to about 7.5 mg/kg in a human, and a dose for mice of 10 mg/kg would work out to about 2.5 mg/kg in a human.

In the treatment of myelosuppression, dithiocarbamic treatment agents of this invention exhibit a rather typical sigmoidal logarithmic dose-response curve, but the placement of this curve with respect to the dose and response axes is surprising. To obtain a typical logarithmic dose-response curve, the percent of surviving stem cells in the test animals is indicated by the ordinate, and the dosage is indicated in 10-fold intervals ($\log_{10}$ dose units) with respect to the abscissa. The resulting plot shows that optimal bone marrow protection can be obtained at dosages well below 50 mg/kg of body weight, and even at well below 30 mg/kg. A response can be observed at extremely low dosages (above submicrogram/kg levels but still below 3 µg/kg, e.g. about 1 µg/kg), and significant protection appears to be obtained, even in mice, at dosages as low as 3 µg/kg, i.e. 0.003 mg/kg. Dosages approaching 30 mg/kg (even in mice) appear to be unnecessarily high in the context of the method of this invention, hence a preferred range for a dosage unit of this invention is about 0.003 to 10 mg/kg of body weight of the mammal. Excellent results are obtained with about 0.01 to about 10 mg/kg, e.g. 0.03-3 mg/kg. The "flat" portion of the sigmoidal curve appears to be reached at dosages as low as 0.3 mg/kg, but it can be desirable to exceed this dosage level in order to provide assurance that efficacy will be high. A particularly preferred upper limit for the human dose appears to be about 10 mg/kg, more preferably 3.0 or even 2.5 mg/kg.

A particularly preferred form of a dosage unit of this invention is obtained by dissolving a dithiocarbamate salt in an aqueous medium (e.g. normal saline), measuring out a dosage unit in the range of 0.001 to 30 mg per kilogram of body weight of the mammal to be treated, and sealing the resulting dosage unit in a vial (e.g. a glass or plastic vial) adapted for use in a conventional intraveneous administration technique. Alternatively, the dosage unit can be dissolved in a conventional plastic intravenous drip bag, in which case the dosage unit can be diluted with an aqueous solution of a typical intravenous administration fluid. (The potential chelating or complexing effects of the dithiocarbamic compound should be taken into account, with respect to such fluids.)

Alternatively, a dosage unit of the dithiocarbamic compound can be extended with a standard solid pharmaceutically acceptable extender (e.g. mannitol) and packaged in dosage unit form for solution later on in a fluid suitable for intravenous administration. Adjuvants, excipients, and the like can be included.

A particularly preferred unit dosage of this invention comprises about 0.01 to about 10 mg/kg of the dithiocarbamic myelosuppression treatment agent, the treatment agent being dissolved in a liquid pharmaceutically acceptable carrier comprising an aqueous medium.

Other suitable pharmaceutically acceptable carriers will occur to those skilled in the art.

When the dosage units are in mg/m$^2$, a useful range is, for example, 0.03-90 mg/m$^2$, more preferably about 1-75 mg/m$^2$, as explained previously.

The principle and practice of this invention is illustrated in the following non-limiting Examples.

EXAMPLES $BDF_1$ mice were used for these Examples. All drugs were administered by intravenous (iv) injection in the tail vein, and Na diethyldithiocarbamate (Na DDTC) was administered at various dosages 3 hours after administration of an anticancer drug. Bone marrow cells were harvested 24 hours after anticancer drug treatment (21 hours after Na DDTC). Toxicity to stem cells was evaluated using the spleen colony (CFU-S) assay; toxicity to granulocyte progenitors was evaluated using an in vitro clonogenic (CFU-GM) assay. To provide controlled studies, mice were randomly divided into four groups of four animals each; one group served as a no-treatment control, one group received Na DDTC alone (the "DDTC group"), one group received anticancer drug alone (the "drug-only group"), and one group received anticancer drug followed by Na DDTC 3 hours later (the "drug and DDTC group"). Twenty-four hours after drug treatment, the mice were killed by cervical dislocation, the femurs were removed, and the marrow cells were flushed out of the bone and counted. For the CFU-S assay, 5-15×10$^4$ cells were injected via the tail vein into recipient mice that had just received a bone marrow lethal dose of radiation. Twelve days after injection of donor marrow cells the mice were killed by cervical dislocation, the spleens were removed, and the colonies of cells growing on the surface of the spleen were counted. The data are normalized to represent the number of colonies formed/$10^5$ cells injected and are reported as the percent of colonies formed compared to the control group. For the CFU-GM assay, $2-4\times10^4$ bone marrow cells from the treated groups were plated on soft agar. After incubating for 7 days, the colonies containing at least 50 cells were counted; in representative experiments, the colonies were removed and the cell type determined. The data are reported as the percent of colonies formed compared to the control group.

The data obtained from the DDTC group and the no-treatment group tends to confirm that Na DDTC has little or no stimulant effect upon healthy bone marrow. That is, Na DDTC has negligible effects on the stem cell and granulocyte precursor populations in normal mouse bone marrow. The colony counts for the DDTC group were within 10% of no-treatment group values for both CFU-S and CFU-GM in all cases. In the drug-only group, dose-dependent toxicity toward both CFU-S and CFU-GM was observed for carmustine (BCNU) and adriamycin. In the drug and DDTC group, Na DDTC provided significant protection against BCNU toxicity to both stem cells and granulocyte progenitors at all doses of BCNU tested. In the case of adriamycin, reduction of toxicity was observed at all doses but was less impressive at the highest adriamycin dose tested.

The situation in the case of mitomycin (an anticancer drug of the antibiotic type) is more complicated because it is particularly difficult to prevent or reverse the myelosuppressive effects of this drug.

Very good results were obtained when the drug+DDTC group was given carboplatin (a platinum-containing anticancer drug) followed by various doses of DDTC. Carboplatin given to the drug-only group resulted in mice having CFU-S values which were only 8% of the control group level. When the CFU-S assay shows 40% or more of the value of the control (no treatment) group, this is considered indicative of very good activity against myelosuppression. The 40% level in the drug+DDTC group was achieved with an iv dose of 30 mg/kg of Na DDTC, but 40% of the control CFU-S level was also achieved with an iv dose of only 0.3 mg/kg of Na DDTC. A 30% level was achieved in the drug+DDT group with a 0.03 mg/kg dose, and a 20% level was obtained with 0.003 mg/kg of Na DDTC. Only when the dosage was decreased still another order of magnitude did the %-of-control level drop to approximately the level observed for the drug-only group (8% of the control level).

In the experiments summarized in this Table (which were conducted according to the procedure described above), the dose of Na DDTC was 300 mg/kg of body weight, which appears to be excessive, but which illustrates the efficacy of dithiocarbamate, vis-a-vis damage from platinum-free drugs. Both in Part A (drug=BCNU) and in Part B (drug=adriamycin), data are given for the "DDTC group", the "drug-only group", and the "drug and DDTC group". These data are set forth in the following Table.

TABLE
EFFECT OF NaDDTC ON DRUG-INDUCED MYELOSUPPRESSION

| Part A<br>Drug: BCNU | Drug<br>Dose<br>(mg/kg) | Mouse<br>Group | CFU-S(%) | CFU-<br>GM(%) |
|---|---|---|---|---|
| | — | DDTC | 102 ± 2 | 102 ± 1 |
| | 20 | Drug-only | 47 ± 6 | 83 ± 2 |
| | 20 | Drug and DDTC | 57 ± 12 | 99 ± 2 |
| | — | DDTC | 101 | 103 ± 2 |
| | 40 | Drug-Only | 30 ± 1 | 43 ± 2 |
| | 40 | Drug and DDTC | 50 ± 1 | 83 ± 2 |
| | — | DDTC | 114 | 102 ± 2 |
| | 65 | Drug-Only | 19 ± 2 | 25 ± 1 |
| | 65 | Drug and DDTC | 49 ± 11 | 64 ± 1 |
| Part B<br>Drug:<br>Adriamycin | — | DDTC | 106 | 102 |
| | 18 | Drug-Only | (21) | 37 ± 6 |
| | 18 | Drug and DDTC | (42) | 45 ± 2 |
| | — | DDTC | — | 102 ± 1 |
| | 24 | Drug-Only | 40 | 32 ± 1 |
| | 24 | Drug and DDTC | 52 | 42 ± 2 |
| | — | DDTC | — | 102 |
| | 32 | Drug-Only | 29 ± 8 | 20 ± 5 |
| | 32 | Drug and DDTC | 57 ± 7 | 28 ± 2 |

We claim:

1. A process for the treatment of myelosuppression resulting from a toxic side effect of a cytotoxic streptomyces-produced antibiotic derivative administered to a human, said process comprising administering about 0.01–10 mg/kg of body weight of said human, of a compound of the formula:

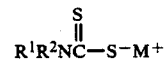

$$R^1R^2N\overset{\overset{S}{\|}}{C}-S^-M^+$$

wherein $M^+$ is a pharmaceutically acceptable cation, and $R^1$ and $R^2$ are the same or different and represent $C_1$-$C_6$ lower aliphatic or hydroxy-substituted lower aliphatic groups.

2. The process of claim 1 wherein the antibiotic derivative is doxorubicin hydrochloride.

* * * * *

UNITED STATES PATENT AND TRADEMARK OFFICE
CERTIFICATE OF CORRECTION

PATENT NO. : 4,938,949

DATED : July 3, 1990

INVENTOR(S) : Borch, et al.

It is certified that error appears in the above-identified patent and that said Letters Patent is hereby corrected as shown below:

At the title page, Assignee, for "University of New York" read --University of Rochester--.

At Col. 8, line 55, for 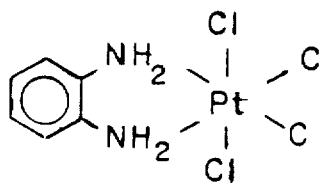 read 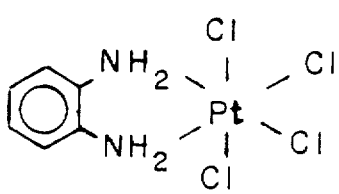

At col. 8, line 58, immediately below the compound structure, insert --where X=OH or $H_2O$--.

At col. 13, line 49, for "drug + DDT group" read --drug + DDTC group--.

Signed and Sealed this

Eleventh Day of August, 1992

Attest:

DOUGLAS B. COMER

Attesting Officer

Acting Commissioner of Patents and Trademarks